(12) United States Patent
Avidor et al.

(10) Patent No.: US 8,764,667 B2
(45) Date of Patent: Jul. 1, 2014

(54) METHOD AND SYSTEM FOR MONITORING SLEEP

(75) Inventors: Yoav Avidor, Tel-Aviv (IL); Daniel Burkhoff, West Harrison, NY (US); Pierre Squara, Enghien-les-Bains (FR); Hanan Keren, Kfar-Saba (IL)

(73) Assignee: Cheetah Medical, Inc., Wilmington, DE (US)

( * ) Notice: Subject to any disclaimer, the term of this patent is extended or adjusted under 35 U.S.C. 154(b) by 1150 days.

(21) Appl. No.: 12/450,022

(22) PCT Filed: Mar. 6, 2008

(86) PCT No.: PCT/IL2008/000309
§ 371 (c)(1),
(2), (4) Date: Sep. 8, 2009

(87) PCT Pub. No.: WO2008/107899
PCT Pub. Date: Sep. 12, 2008

(65) Prior Publication Data
US 2010/0031959 A1    Feb. 11, 2010

Related U.S. Application Data

(63) Continuation-in-part of application No. 11/889,395, filed on Aug. 13, 2007.

(60) Provisional application No. 60/905,313, filed on Mar. 7, 2007.

(51) Int. Cl.
*A61B 5/02* (2006.01)

(52) U.S. Cl.
USPC .......................... 600/483; 600/302; 600/526

(58) Field of Classification Search
USPC ........................................ 600/302, 483, 526
See application file for complete search history.

(56) References Cited

U.S. PATENT DOCUMENTS

| | | | |
|---|---|---|---|
| 3,340,867 | A | 9/1967 | Kubicek et al. |
| 3,851,641 | A | 12/1974 | Toole et al. |
| 3,874,368 | A | 4/1975 | Asrican |
| 3,914,999 | A | 10/1975 | Grandchamp |
| 4,094,309 | A | 6/1978 | Grzenia |
| 4,153,048 | A | 5/1979 | Magrini |
| RE30,101 | E | 9/1979 | Kubicek et al. |

(Continued)

FOREIGN PATENT DOCUMENTS

| | | |
|---|---|---|
| WO | WO 96/32883 | 10/1996 |
| WO | WO 97/11638 | 4/1997 |

(Continued)

OTHER PUBLICATIONS

Examiner's Report Dated Nov. 15, 2010 From the Australian Government, IP Australia Re. Application No. 2006215274.

(Continued)

*Primary Examiner* — Navin Natnithithadha
*Assistant Examiner* — Etsub Berhanu

(57) ABSTRACT

A method of monitoring sleep of a sleeping subject is disclosed. The method comprises determining a phase shift of input radiofrequency signals received from the subject during sleep relative to output radiofrequency signals transmitted to the subject during sleep, calculating cardiac output based on the phase shift, and using the cardiac output for identifying sleep apnea events.

26 Claims, 9 Drawing Sheets

(56) References Cited

U.S. PATENT DOCUMENTS

| | | | |
|---|---|---|---|
| 4,437,469 A | 3/1984 | Djordjevich et al. | |
| 4,450,527 A | 5/1984 | Sramek | |
| 4,537,200 A | 8/1985 | Widrow | |
| 4,610,254 A | 9/1986 | Morgan et al. | |
| 4,705,049 A | 11/1987 | John | |
| 4,781,201 A * | 11/1988 | Wright et al. | 600/484 |
| 4,803,431 A | 2/1989 | Sano et al. | |
| 4,805,621 A | 2/1989 | Heinze et al. | |
| 4,852,580 A | 8/1989 | Wood | |
| 4,870,578 A | 9/1989 | Vysin et al. | |
| 4,888,558 A | 12/1989 | Hereikson | |
| 4,926,868 A | 5/1990 | Larsen | |
| 4,953,556 A | 9/1990 | Evans | |
| 5,058,583 A | 10/1991 | Geddes et al. | |
| 5,158,093 A | 10/1992 | Shvartz et al. | |
| 5,178,154 A | 1/1993 | Ackman et al. | |
| 5,309,917 A | 5/1994 | Wang et al. | |
| 5,316,004 A | 5/1994 | Chesney et al. | |
| 5,423,326 A | 6/1995 | Wang et al. | |
| 5,469,859 A | 11/1995 | Tsoglin et al. | |
| 5,503,157 A | 4/1996 | Sramek | |
| 5,505,209 A | 4/1996 | Reining | |
| 5,529,072 A | 6/1996 | Sramek | |
| 5,615,689 A | 4/1997 | Kotler | |
| 5,642,734 A | 7/1997 | Ruben et al. | |
| 5,685,316 A | 11/1997 | Shookin et al. | |
| 5,817,030 A | 10/1998 | Tarjan et al. | |
| 5,913,826 A | 6/1999 | Blank | |
| 6,015,393 A | 1/2000 | Hovland et al. | |
| 6,053,873 A | 4/2000 | Govari et al. | |
| 6,073,039 A | 6/2000 | Berson | |
| 6,076,015 A | 6/2000 | Hartley et al. | |
| 6,142,941 A | 11/2000 | Benhalima et al. | |
| 6,298,267 B1 | 10/2001 | Rosborough et al. | |
| 6,304,773 B1 | 10/2001 | Taylor et al. | |
| 6,339,722 B1 | 1/2002 | Heethaar et al. | |
| 6,413,223 B1 | 7/2002 | Yang et al. | |
| 6,440,082 B1 | 8/2002 | Joo et al. | |
| 6,485,431 B1 | 11/2002 | Campbell et al. | |
| 6,496,732 B1 | 12/2002 | Wallace | |
| 6,511,438 B2 | 1/2003 | Bernstein et al. | |
| 6,577,897 B1 | 6/2003 | Shurubura et al. | |
| D625,823 S | 10/2010 | Schneider et al. | |
| 8,414,498 B2 | 4/2013 | Keren et al. | |
| 2002/0143368 A1 | 10/2002 | Bakels et al. | |
| 2002/0193689 A1 | 12/2002 | Bernstein et al. | |
| 2003/0083702 A1 | 5/2003 | Stadler et al. | |
| 2003/0109790 A1 | 6/2003 | Stickney et al. | |
| 2003/0120170 A1 | 6/2003 | Zhu et al. | |
| 2003/0158584 A1 | 8/2003 | Cates et al. | |
| 2003/0187341 A1 | 10/2003 | Sackner et al. | |
| 2003/0199779 A1 | 10/2003 | Muhlenberg et al. | |
| 2004/0102908 A1 | 5/2004 | Larson et al. | |
| 2004/0133123 A1 | 7/2004 | Leonhardt et al. | |
| 2005/0004609 A1 | 1/2005 | Stahmann et al. | |
| 2005/0043763 A1 | 2/2005 | Marcovecchio et al. | |
| 2005/0124901 A1 | 6/2005 | Misczynski et al. | |
| 2005/0143634 A1 | 6/2005 | Baker et al. | |
| 2005/0192488 A1 | 9/2005 | Bryenton et al. | |
| 2005/0202789 A1 | 9/2005 | Tanabe et al. | |
| 2005/0217674 A1 | 10/2005 | Burton et al. | |
| 2006/0085048 A1 | 4/2006 | Cory et al. | |
| 2006/0122540 A1 | 6/2006 | Zhu et al. | |
| 2006/0200033 A1 | 9/2006 | Keren et al. | |
| 2007/0088221 A1 | 4/2007 | Stahmann | |
| 2007/0191688 A1* | 8/2007 | Lynn | 600/300 |
| 2008/0154116 A1 | 6/2008 | Duensing et al. | |
| 2008/0255433 A1* | 10/2008 | Prough et al. | 600/301 |
| 2009/0048497 A1* | 2/2009 | Keren | 600/301 |
| 2010/0069765 A1 | 3/2010 | Keren | |
| 2011/0218419 A1 | 9/2011 | Keren et al. | |
| 2013/0144177 A1 | 6/2013 | Keren et al. | |

FOREIGN PATENT DOCUMENTS

| | | |
|---|---|---|
| WO | WO 2004/098376 | 11/2004 |
| WO | WO 2004/112606 | 12/2004 |
| WO | WO 2006/087696 | 8/2006 |
| WO | WO 2007096054 A2 * | 8/2007 |
| WO | WO 2008/102362 | 8/2008 |
| WO | WO 2008/107899 | 9/2008 |
| WO | WO 2008/129535 | 10/2008 |
| WO | WO 2009/022330 | 2/2009 |

OTHER PUBLICATIONS

Response Dated Dec. 29, 2010 to Notice of Reason for Rejection of Sep. 17, 2010 From the Japanese Patent Office Re. Application No. 2006-507622.

Communication Pursuant to Article 94(3) EPC Dated Jan. 26, 2011 From the European Patent Office Re.: Application No. 04731993.4.

Communication Pursuant to Article 94(3) EPC Dated Feb. 13, 2012 From the European Patent Office Re. Application No. 08789780.7.

Requisition by the Examiner Dated Jan. 9, 2012 From the Canadian Intellectual Property Office Re. Application No. 2,525,443.

Communication Pursuant to Article 94(3) EPC Dated Feb. 13, 2012 From the European Patent Office Re.: Application No. 08710233.1.

Communication Pursuant to Article 94(3) EPC Dated Feb. 13, 2012 From the European Patent Office Re. Application No. 08719934.5.

Response Dated Jun. 3, 2010 to Communication Pursant to Article 94(3) EPC of Feb. 12, 2010 From the European Patent Office RE.: Application No. 08738211.5.

Restriction Official Action Dated Jun. 7, 2012 From the US Patent and Trademark Office Re. U.S. Appl. No. 11/889,395.

Official Action Dated Jun. 22, 2010 From the US Patent and Trademark Office Re.: U.S. Appl. No. 10/556,483.

Response Dated Jun. 28, 2010 to Communication Pursuant to Article 94(3) EPC of Dec. 29, 2009 From the European Patent Office Re.: Application No. 08710233.1.

Response Dated Jul. 4, 2010 to Invitation Pursuant to Rule 62a(1) EPC of Jun. 10, 2010 From the European Patent Office Re. Application No. 06700959.7.

Official Action Dated Jul. 10, 2012 From the US Patent and Trademark Office Re. U.S. Appl. No. 12/527,697.

Translation of Official Querry Dated Jul. 1, 2011 From the Japanese Patent Office Re. Application No. 2006-507622.

Response Dated Jul. 25, 2011 to Communication Pursuant to Article 94(3) EPC of Jan. 26, 2011 From the European Patent Office Re.: Application No. 04731993.4.

Patent Examination Report Dated Aug. 1, 2012 From the Australian Government, IP Australia Re. Application No. 2008242145.

Official Action Dated Aug. 9, 2012 From the US Patent and Trademark Office Re. U.S. Appl. No. 11/889,395.

Official Action Dated Aug. 31, 2011 From the US Patent and Trademark Office Re. U.S. Appl. No. 11/884,227.

Response Dated Sep. 11, 2011 to Official Querry Dated Jul. 1, 2011 From the Japanese Patent Office Re. Application No. 2006-507622.

Translation of Notice of Reason for Rejection Dated Sep. 17, 2010 From the Japanese Patent Office Re. Application No. 2006-507622.

Communication Pursuant to Article 94(3) EPC Dated Oct. 20, 2010 From the European Patent Office Re. Application No. 08719934.5.

Official Action Dated Nov. 2, 2011 From the US Patent and Trademark Office Re. U.S. Appl. No. 11/884,227.

Delpierre et al. "Doppler Effect With Sound", Electronic Science Tutor, Retrieved From the Internet, 5 P., Oct. 18, 2011.

Ellis "Introduction to Mixers", Retrieved From the Internet, 9 P., 1999.

Response Dated Nov. 17, 2011 to Examiner's Report of Nov. 15, 2010 From the Australian Government, IP Australia Re. Application No. 2006215274.

Response Dated Jul. 21, 2010 to Notice of Reason for Rejection of Apr. 6, 2010 From the Japanese Patent Office Re. Application No. 2006-507622.

Translation of Notice of Reason for Rejection Dated Apr. 6, 2010 From the Japanese Patent Office Re. Application No. 2006-507622.

(56) References Cited

OTHER PUBLICATIONS

Official Action Dated Aug. 2, 2012 From the US Patent and Trademark Office Re. U.S. Appl. No. 11/884,227.
Official Action Dated Jul. 24, 2012 From the US Patent and Trademark Office Re. U.S. Appl. No. 12/596,483.
Requisition by the Examiner Dated Jul. 24, 2012 From the Canadian Intellectual Property Office Re. Application No. 2,525,443.
Response Dated Sep. 12, 2011 to Official Action of Aug. 31, 2011 From the US Patent and Trademark Office Re. U.S. Appl. No. 11/884,227.
Communication Under Rule 71(3) EPC Dated Oct. 7, 2011 From the European Patent Office Re.: Application No. 08738211.5.
Response Dated Sep. 21, 2010 to Official Action of Jun. 22, 2010 From the US Patent and Trademark Office Re.: U.S. Appl. No. 10/556,483.
Written Opinion Dated Mar. 22, 2005 From the International Searching Authority Re.: Application No. PCT/I104/00395.
Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h Col., § 3-p. 557, r-h Col., § 1, p. 557, 1-h Col., § 3, p. 558, 1-h Col., § 2-r-h Col., § 1, Fig.3.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Communication Pursuant to Article 94(3) EPC Dated Feb. 12, 2010 From the European Patent Office Re.: Application No. 08738211.5.
Response Dated Apr. 6, 2010 to Official Action of Oct. 6, 2009 From the US Patent and Trademark Office Re.: U.S. Appl. No. 10/556,483.
Communication Pursuant to Article 94(3) EPC Dated May 14, 2012 From the European Patent Office Re.: Application No. 04731993.4.
Requisition by the Examiner Dated May 30, 2012 From the Canadian Intellectual Property Office Re. Application No. 2,597,264.
Invitation Pursuant to Rule 62a(1) EPC Dated Jun. 10, 2010 From the European Patent Office Re. Application No. 06700959.7.
Communication Pursuant to Article 94(3) EPC Dated Jul. 8, 2009 From the European Patent Office Re.: Application No. 04731993.4.
Communication Relating to the Results of the Partial International Search Dated Dec. 5, 2008 From the International Searching Authority Re.: Application No. PCT/IL2008/001105.
International Preliminary Report on Patentability Dated Nov. 4, 2009 From the International Preliminary Examining Authority Re.: Application No. PCT/IL2008/001105.
International Preliminary Report on Patentability Dated Aug. 16, 2007 From the International Preliminary Examining Authority Re.: Application No. PCT/IL06/00075.
International Preliminary Report on Patentability Dated Sep. 17, 2009 From the International Bureau of WIPO Re.: Application No. PCT/IL2008/000309.
International Preliminary Report on Patentability Dated Nov. 18, 2008 From the International Preliminary Examing Authority Re.: Application No. PCT/IL04/00395.
International Preliminary Report on Patentability Dated Aug. 26, 2009 From the International Bureau of WIPO Re.: Application No. PCT/IL2008/000233.
International Preliminary Report on Patentability Dated Oct. 29, 2009 From the International Bureau of WIPO Re.: Application No. PCT/IL2008/000509.
International Search Report Dated Aug. 5, 2008 From the International Searching Authority Re.: Application No. PCT/IL2008/000309.
International Search Report Dated Dec. 6, 2006 From the International Searching Authority Re.: Application No. PCT/IL06/00075.
International Search Report Dated Mar. 22, 2005 From the International Searching Authority Re.: Application No. PCT/IL04/00395.
International Search Report Dated Mar. 27, 2009 From the International Searching Authority Re.: Application No. PCT/IL2008/001105.
International Search Report Dated Jul. 28, 2008 From the International Searching Authority Re.: Application No. PCT/IL2008/000233.
Office Action Dated Dec. 12, 2008 From the State Intellectual Property Office of the People's Republic of China Re.: Application No. 200680012560.2.
Office Action Dated Apr. 24, 2009 From the State Intellectual Property Office of the People's Republic of China Re.: Application No. 200480019436.X.
Office Action Dated Jul. 24, 2009 From the State Intellectual Property Office of the People's Republic of China Re.: Application No. 200680012560.2 and Its Translation Into English.
Official Action Dated Oct. 6, 2009 From the US Patent and Trademark Office Re.: U.S. Appl. No. 10/556,483.
Official Action Dated Feb. 18, 2009 From the US Patent and Trademark Office Re.: U.S. Appl. No. 10/556,483.
Response Dated Nov. 8, 2009 to Communication Pursuant to Article 94(3) EPC of Jul. 8, 2009 From the European Patent Office Re.: Application No. 04731993.4.
Supplementary Partial European Search Report Dated Apr. 9, 2009 From the European Patent Office Re.: Application No. 04731993.4.
Translation of the Official Action Dated Dec. 12, 2008 From the State Intellectual Property Office of the People's Republic of China Re.: Application No. 200680012560.2.
Written Opinion Dated Aug. 5, 2008 From the International Searching Authority Re.: Application No. PCT/IL2008/000309.
Written Opinion Dated Dec. 6, 2006 From the International Searching Authority Re.: Application No. PCT/IL06/00075.
Written Opinion Dated Mar. 27, 2009 From the International Searching Authority Re.: Application No. PCT/IL2008/001105.
Written Opinion Dated Jul. 28, 2008 From the International Searching Authority Re.: Application No. PCT/IL2008/000233.
Goovaerts et al. "A Wideband High Common Mode Rejection Ratio Amplifier for Multifrequency Impedance Measurement", Medical and Biological Engineering and Computing, XP000784850, 36(6): 761-767, Nov. 1, 1998. Section 2.2 'Lock-in Measurement', p. 761, p. 763, col. 2, Figs.2, 3.
Jellinek et al. "Right Atrial Pressure Predicts Hemodynamic Response to Apneic Positive Airway Pressure", Critical Care Medicine, XP002488470, 28(3): 672-678, Mar. 2000. Database MEDLINE [Online], US National Library of Medicine, Database Accession No. NLM10752813. Abstract.
Kubicek et al. "The Minnesota Impedance Cardiograph—Theory and Applications", Biomedical Engineering, XP001051054, 9(9): 410-416, Sep. 1, 1974. p. 411, Middle Col., Figs.1, 2.
Lele et al. "Exercise Capacity in Hypertrophic Cardiomyopathy. Role of Stroke Volume Limitation, Heart Rate, and Diastolic Filling Characteristics", Circulation, XP002487808, 92(10): 2886-2894, 1995.
Lin et al. "Effects of Hypercapnia, Hypoxia, and Rebreathing on Circulatory Response to Apnea", Journal of Applied Physiology Respiratory Environmental and Exercise Physiology, XP008094195, 54(1): 172-177, 1983.
Miyamoto et al. "Cardiorespiratory Dynamics During Sinusoidal and Impulse Exercise in Man", Japanese Journal of Physiology, XP008094022, 33(6): 971-986, 1983.
Myers et al. "Cardiac Output and Cardiopulmonary Responses to Exercise in Heart Failure: Application of A New Bio-Resistance Device", Journal of Cardiac Failure, XP0022287174, 13(8): 629-636, Oct. 6, 2007.
Newman et al. "The Non-Invasive Assessment of Stroke Volume and Cardiac Output by Impedance Cardiography: A Review", Aviation Space and Environmental Medicine, XP008093991, 70(8): 780-789, Aug. 1999.
Schumacker et al. "Oxygen Delivery and Uptake Relationships in Patients With Aortic Stenosis", American Journal of Respiratory and Critical Care Medicine, XP002488468, 149(5): 1123-1131, May 1994. Database EMBASE [Online], Database Accession No. EMB-1994152503, 1994. Abstract.
Stoohs et al. "Cardiovascular Changes Associated With Obstructive Sleep Apnea Syndrome", Journal of Applied Physiology,

(56) References Cited

OTHER PUBLICATIONS

XP002488467, 72(2): 583-589, 1992. Database Biosis [Online], Biosciences Information Service, Database Accession No. PREV199293105800, 1992. Abstract.
Tolle et al. "Reduced Stroke Volume Related to Pleural Pressure in Obstructive Sleep Apnea", Journal of Applied Physiology Respiratory Environmental and Exercise Physiology, XP002488469, 55(6): 1718-1724, 1983. Database BIOSIS [Online], Biosciences Information Service, Database Accession No. PREV198477063246, 1883. Abstract.
Communication Pursuant to Article 94(3) EPC Dated Dec. 29, 2009 From the European Patent Office Re.: Application No. 08710233.1.
Notice of Allowance Dated Jan. 30, 2013 From the US Patent and Trademark Office Re.: U.S. Appl. No. 10/556,483.
Notice of Allowance Dated May 10, 2013 From the US Patent and Trademark Office Re. U.S. Appl. No. 12/596,483.
Applicant-Initiated Interview Summary Dated Sep. 17, 2012 From the US Patent and Trademark Office Re. U.S. Appl. No. 11/884,227.
Communication Under Rule 71(3) EPC Dated Oct. 17, 2012 From the European Patent Office Re. Application No. 08789780.7.
Patent Examination Report Dated Nov. 30, 2012 From the Australian Government, IP Australia Re. Application No. 2008288084.
Official Action Dated Apr. 30, 2013 From the US Patent and Trademark Office Re. U.S. Appl. No. 11/889,395.
Notice of Allowance Dated Oct. 25, 2012 From the US Patent and Trademark Office Re. U.S. Appl. No. 11/884,227.
Official Action Dated Oct. 15, 2012 From the US Patent and Trademark Office Re. U.S. Appl. No. 12/673,037.
Notice of Allowability Dated Nov. 21, 2012 From the US Patent and Trademark Office Re. U.S. Appl. No. 11/884,227.
Official Action Dated Apr. 9, 2013 From the US Patent and Trademark Office Re. U.S. Appl. No. 12/527,697.
Communication Under Rule 71(3) EPC Dated Jan. 16, 2014 From the European Patent Office Re. Application No. 04731993.4.
Official Action Dated Jun. 26, 2013 From the US Patent and Trademark Office Re. U.S. Appl. No. 12/527,697.
Restriction Official Action Dated Jul. 3, 2013 From the US Patent and Trademark Office Re. U.S. Appl. No. 13/757,920.
Official Action Dated Aug. 12, 2013 From the US Patent and Trademark Office Re. U.S. Appl. No. 13/757,920.
Brief Communication for Oral Proceedings on Dec. 10, 2013 Dated Dec. 3, 2013 From the European Patent Office Re. Application No. 04731993.4.
Scofield "A Frequency-Domain Description of A Lock-in-Amplifier", American Journal of Physics, XP009097728, 62(2): 129-133, Feb. 1, 1994.
Requisition by the Examiner Dated Dec. 6, 2013 From the Canadian Intellectual Property Office Re. Application No. 2,597,264.
Notice of Allowance Dated Apr. 1, 2014 From the US Patent and Trademark Office Re. U.S. Appl. No. 12/673,037.
Official Action Dated Mar. 10, 2014 From the US Patent and Trademark Office Re. U.S. Appl. No. 11/889,395.
Official Action Dated May 2, 2014 From the US Patent and Trademark Office Re. U.S. Appl. No. 13/757,920.

* cited by examiner

METHOD AND SYSTEM FOR MONITORING SLEEP

RELATED APPLICATIONS

This Application is a National Phase of PCT Patent Application No. PCT/IL2008/000309 having International filing date of Mar. 6, 2008, which is a continuation-in-part of U.S. patent application Ser. No. 11/889,395 filed on Aug. 13, 2007.

PCT Patent Application No. PCT/IL2008/000309 also claims the benefit of U.S. Provisional Patent Application No. 60/905,313 filed on Mar. 7, 2007.

The contents of the above Applications are all incorporated herein by reference.

FIELD AND BACKGROUND OF THE INVENTION

The present invention, in some embodiments thereof, relates to medical application and, more particularly, but not exclusively, to a method and system for monitoring sleep.

Apnea is a Greek word meaning "without breath" which is used in the literature to describe a condition of a temporary pause in breathing. Sleep apnea refers to the temporary cessation of breathing during sleep. Sleep apneas have been classified into three types: obstructive sleep apnea (OSA), central sleep apnea (CSA) and mixed sleep apnea (MSA). The difference between obstructive sleep apnea and central sleep apnea is that in obstructive sleep apnea the breathing passageways are blocked, while in central sleep apnea the neural drive to respiratory muscles is transiently abolished but the passageways can still be open. In central sleep apnea the lungs form a reservoir for air flow even though the individual is not breathing.

Mixed sleep apnea consists of a central sleep apnea component and an obstructive sleep apnea component. In mixed sleep apnea, the obstructive component typically follows the central component. The most common type of sleep apnea is obstructive sleep apnea.

Also known are obstructive sleep hypopnea, which is a milder form of obstructive apnea characterized by partial obstruction of the upper airway passages, and central sleep hypopnea, which is a milder form of central sleep apnea characterized by shallow breathing while the upper airway are open.

An apnea event generally leads to a progressive-type asphyxia until the individual is briefly aroused from the sleeping state, thereby restoring airway patency or respiratory muscles activity thereby restoring airflow to the lung. Consequently, sleep of individuals diagnosed with sleep apnea is fragmented and of poor quality.

Sleep apneas, particularly of the obstructive type, are recognized as life-threatening conditions. Individuals with sleep apnea have an increased risk of suffocating during sleep or during surgery requiring general anesthesia.

Sleep apnea is diagnosed using a test called Polysomnography (PSG), which involves the patient sleeping in a sleep lab connected to various measurement instruments. The test provides an Apnea/Hypopnea Index (AHI) which drives a diagnosis of sleep apnea along with severity.

When an individual is diagnosed with sleep apnea, the individual may be prescribed a therapeutic regime involving the use of a Continuous Positive Airway Pressure (CPAP) device. The CPAP device works by delivering a steady flow of air through a soft, pliable mask worn over the individual's nose. The CPAP device essentially pressurizes the throat of the individual thereby preventing the collapse of the soft tissue and keeping the airways open and allowing the individual to breathe uninterrupted during sleep.

For more severe cases of OSA, surgery such as laser assisted uvuloplasty is used to provide a partial treatment. Additional types of treatments are disclosed in U.S. Pat. Nos. 5,988,171, 6,250,307, 6,523,542, 6,431,174 and 6,601,584.

SUMMARY OF THE INVENTION

According to an aspect of some embodiments of the present invention there is provided a method of monitoring sleep of a sleeping subject using output radiofrequency signals transmitted to the subject during sleep and input radiofrequency signals received from the subject during sleep. The method comprises determining a phase shift of the input radiofrequency signals relative to the output radiofrequency signals, calculating cardiac output based on the phase shift, and using the cardiac output for identifying sleep apnea events.

According to an aspect of some embodiments of the present invention there is provided a method of monitoring sleep of a sleeping subject. The method comprises transmitting output radiofrequency signals to the subject during sleep, receiving input radiofrequency signals from the subject during sleep, and executing the method described above.

According to some embodiments of the present invention the method further comprises supplementing the cardiac output with blood oxygen content which can be measured, for example, via pulse oximetry. In these embodiments, the identification of the sleep apnea events can be based on the cardiac output and the blood oxygen content. For example, total oxygen delivery can be estimated as further detailed hereinunder.

According to some embodiments of the present invention the method further comprises estimating or receiving hemoglobin concentration of the sleeping subject. In some embodiments, the hemoglobin concentration is used for estimating oxygen content.

According to some embodiments of the present invention the method further comprises estimating total oxygen delivery and generating a wakening signal when an estimated value is below a predetermined threshold.

According to some embodiments of the invention the identification of the sleep apnea events is further based on the estimated value of the total oxygen delivery.

According to some embodiments of the present invention the method further comprises controlling positive airway pressure delivered to the subject based on the estimated value of the total oxygen delivery. In various exemplary embodiments of the invention the control of airway pressure is in a closed loop feedback with the estimation of total oxygen delivery. Thus, the method controls the delivered positive airway pressure such as to ensure that the estimated amount of total oxygen delivery is above a predetermined threshold, or within a predetermined range.

According to some embodiments of the present invention the method further comprises reducing or eliminating amplitude modulation of the input radiofrequency signals so as to provide input radiofrequency signals of substantially constant envelope.

According to some embodiments of the present invention the method further comprises mixing the output radiofrequency signals and the input radiofrequency signals so as to provide a mixed radiofrequency signal, and filtering out a portion of the mixed radiofrequency signal so as to substantially increase a signal-to-noise ratio of a remaining portion of the mixed radiofrequency signal.

According to some embodiments of the present invention the method further comprises applying a dynamically variable filter.

According to an aspect of some embodiments of the present invention there is provided apparatus for monitoring sleep of a sleeping subject using output radiofrequency signals transmitted to the subject during sleep and input radiofrequency signals received from the subject during sleep. The apparatus comprises a phase shift determinator configured for determining a phase shift of the input radiofrequency signals relative to the output radiofrequency signals, a cardiac output calculator configured for calculating cardiac output based on the phase shift, and a sleep apnea identification unit configured for identifying sleep apnea events based on the cardiac output.

According to an aspect of some embodiments of the present invention there is provided a system for monitoring sleep of a sleeping subject. The system comprises a radiofrequency generator for generating output radiofrequency signals, a plurality of electrodes designed for transmitting the output radiofrequency signals to the subject and for sensing input radiofrequency signals from the subject, and the monitoring apparatus described above.

According to some embodiments of the present invention the system further comprises a blood oxygen measuring device, wherein the sleep apnea identification unit is configured to identify the sleep apnea events based on the cardiac output and the blood oxygen content.

According to some embodiments of the present invention the apparatus further comprises a total oxygen delivery estimator configured for estimating total oxygen delivery.

According to some embodiments of the invention the sleep apnea identification unit is configured to identify the sleep apnea events based on an estimated value of the total oxygen delivery and the cardiac output.

According to some embodiments of the invention the system comprises a respiratory therapy device, such as, but not limited to, a continuous positive airway pressure (CPAP) device.

According to some embodiments of the invention the apparatus comprises a closed-loop control unit which receives the estimated value of total oxygen delivery from the total oxygen delivery estimator and controls the pressure delivered by the respiratory therapy device based on the estimated value. In various exemplary embodiments of the invention the closed-loop control unit controls the pressure to ensure that the estimated value of total oxygen delivery is above a predetermined threshold or within a predetermined range.

According to some embodiments of the present invention the apparatus further comprises an envelope elimination unit designed and configured for reducing or eliminating amplitude modulation of the input radiofrequency signals so as to provide input radiofrequency signals of substantially constant envelope.

According to some embodiments of the present invention the apparatus further comprises: a mixer configured for mixing the output radiofrequency signals and the input radiofrequency signals, to provide a mixed radiofrequency signal; and a radiofrequency filter for filtering out a portion of the mixed radiofrequency signal so as to substantially increase a signal-to-noise ratio of a remaining portion of the mixed radiofrequency signal.

According to some embodiments of the present invention the apparatus further comprises a filtering unit configured for filtering the input signals using dynamically variable filter.

According to some embodiments of the present invention the cardiac output is calculated using a linear relationship between the phase shift and the cardiac output.

According to some embodiments of the present invention the dynamically variable filter is adapted in response to a change in a physiological condition of the subject.

According to some embodiments of the invention the physiological condition is a heart rate of the subject.

According to some embodiments of the invention a lower frequency bound characterizing the filter is about $0.9*(HR/60)$ Hz at all times, wherein the HR is the heart rate in units of beats per minute.

According to some embodiments of the invention an upper frequency bound characterizing the filter is about $6+1.5*[(HR/60)-1]$ Hz at all times, wherein the HR is the heart rate in units of beats per minute.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
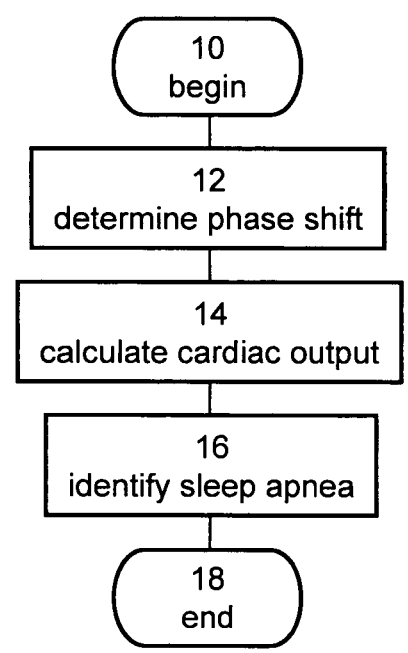
FIG. 1 is a flowchart diagram of a method suitable for monitoring sleep of a sleeping subject according to various exemplary embodiments of the present invention.

The present invention, in some embodiments thereof, relates to medical application and, more particularly, but not exclusively, to a method, apparatus and system for monitoring sleep.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Computer programs implementing the method according to embodiments of the present invention can commonly be distributed to users on a distribution medium such as, but not limited to, a floppy disk, CD-ROM and flash memory cards. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method, apparatus and system of the present embodiments are particularly useful for the analysis of sleep. Yet, the use of the present embodiments in other situations, such as general anesthesia or the like, is not excluded from the scope of the present invention.

The method, apparatus and system of the present embodiments are suitable for identifying sleep apnea events caused by blockage or partial blockage of breathing passageways and/or by lack or reduced neural drive to the respiratory muscles.

The recurrent episodes of nocturnal asphyxia, cerebral hypoxia and arousal from sleep that characterize sleep apnea lead to a series of secondary physiologic events, which in turn give rise to various clinical complications.

Some manifestations are neuropsychiatric and behavioral disturbances that generally arise from the fragmentation of sleep and loss of slow-wave sleep induced by the recurrent arousal responses. Manifestations of neuropsychiatric and behavioral disturbances include excessive daytime sleepiness, intellectual impairment, memory loss, personality disturbances and impotence. Other manifestations are cardiorespiratory in nature and are thought to arise from the recurrent episodes of nocturnal asphyxia. Cardiorespiratory manifestations include bradycardia followed by tachycardia, tachyarrhythmia.

Central sleep apnea may also lead to secondary physiological and clinical consequences. Central sleep apnea can be identified in a wide spectrum of individuals with medical, neurological and/or neuromuscular disorders associated with diurnal alveolar hypoventilation or periodic breathing. In less severe cases, central sleep apnea events particularly occur at sleep onset and in REM sleep. In clinically significant central sleep apnea, events occur also in other sleep stages. Manifestations of central sleep apnea may include alveolar hypoventilation syndrome, daytime hypercapnia, hypoxemia, recurrent respiratory failure, polycythemia, pulmonary hypertension and right-sided heart failure.

Chronic sleep apnea may lead to various serious complications such as heart failure. The mechanism by which sleep apnea patients develop heart failure relates to build up of intrathoracic pressure. During an apnea event the pressure in the chest builds due to deposition of carbon dioxide in the lungs with no ventilation. The rising carbon dioxide pressure increases thoracic pressure and reduces the venous return to the right heart resulting in a reduced or failure of left ventricular function. Increased left ventricular after load, recurrent nocturnal hypoxemia and elevated sympathoadrenal activity also contribute to the reduced left ventricular function.

It was found by the present inventors that apnea events can be identified by monitoring cardiac output. Specifically, since a reduced left ventricular filling is accompanied by a drop in cardiac output, an apnea event can be identified when the cardiac output is reduced.

Referring now to the drawings, FIG. 1 is a flowchart diagram of a method suitable for monitoring sleep of a sleeping subject according to various exemplary embodiments of the present invention.

It is to be understood that, unless otherwise defined, the method steps described hereinbelow can be executed either contemporaneously or sequentially in many combinations or orders of execution. Specifically, the ordering of the flowcharts diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method is particularly useful for monitoring sleep using output radiofrequency signals transmitted to the subject during sleep and input radiofrequency signals received from the subject during sleep.

The method begins at step 10 and continues to step 12 in which a phase shift of the input radiofrequency signals relative to the output radiofrequency signals is determined. The method continues to step 14 in which a cardiac output is calculated, based on the phase shift. The method continues to step 16 in which the cardiac output is used for identifying sleep apnea events.

The method ends at step 18.

Before providing a further detailed description of the method and apparatus for monitoring sleep, as delineated hereinabove and in accordance with some embodiments of the present invention, attention will be given to the advantages and potential applications offered thereby.

The present inventors conducted experiments in which cardiac output response to positive end expiratory pressure was evaluated. Without being bound to any theory, it is postulated that positive end expiratory pressure can be surrogate for sleep apnea because it creates positive thoracic pressure induced by mechanical ventilation in anesthetized subjects in intensive care units. The pressure dynamics in positive end expiratory pressure are similar to those observed during an apnea episode.

Figure 2:
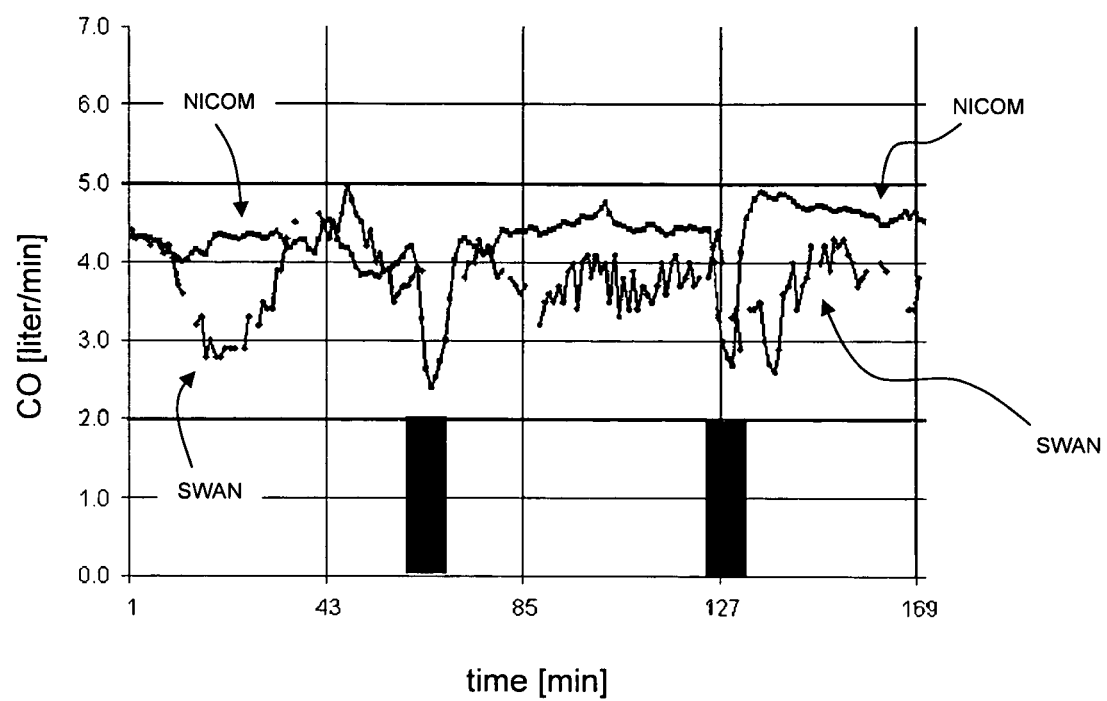
FIG. 2 shows cardiac output response of a female subject during positive end expiratory pressure treatment, as measured according to some embodiments of the present invention and further measured using a pulmonary artery catheter.

FIG. 2 shows cardiac output response of a female subject during positive end expiratory pressure treatment in intensive care unit. The cardiac output was measured using a conventional pulmonary artery catheter (Swan-Ganz catheter), as well as non-invasively using the phase shift of the input relative to output radiofrequency signals according to various embodiments of the present invention. Measurements performed according to the present embodiments are designated NICOM (Non-Invasive Cardiac Output Monitoring), and measurements performed using the pulmonary artery catheter are designated SWANG. Onsets of positive end expiratory pressure are marked by dark rectangles.

As shown in FIG. 2, significant drops in cardiac output are correlated with the onset of positive end expiratory pressure. Thus, apnea events can be identified when the level of cardiac output is reduced.

In various exemplary embodiments of the invention an apnea event is identified when the cardiac output as calculated using the phase shift between the radiofrequency signals is reduced by at least 30%, more preferably at least 40%, more preferably at least 50% over a time period of less than two minutes. In embodiments in which arterial oxygen saturation ($SPO_2$) is monitored, a lower threshold of comprises reduction can be employed. For example, an apnea event can be identified when the calculated cardiac output is reduced by at least 25% and the value of $SPO_2$ is significantly decreased (say, by more than 40%).

Traditionally, sleep apnea is diagnosed via PSG. The logistics and cost of PSG, however significantly complicate the ability to diagnose the condition. The present embodiments provide a screening modality which can be used in small facilities and at home. The present embodiments allow fast screening of many subjects, by providing each subject with a system operable to execute selected steps of the method described herein. The present embodiments also allow screening out subjects for which sleep study is no required, thereby saving significant resources.

The present embodiments can also be employed by subjects who already been diagnosed with sleep apnea and for whom a CPAP device has been prescribed. Specifically, the present embodiments can be used as a supplement to a conventional treatment (e.g., a CPAP device) so as to assess the efficacy of treatment. For example, the present embodiments can be used for determining whether or not a sufficient amount of oxygen is delivered to vital organs such as the brain, heart and kidneys. It is recognized that even when a CPAP device pushes air to the lungs, oxygen delivery from the cardiopulmonary system to vital tissues is not guaranteed. For example, a significant drop in cardiac output may result in insufficient oxygen delivery even when the CPAP device increases the oxygen content in the blood. In this case, a system according to some embodiments of the present invention can signal the CPAP device to increase the positive airway pressure and/or generate a wakening signal sensible by the sleeping subject.

Figure 3:
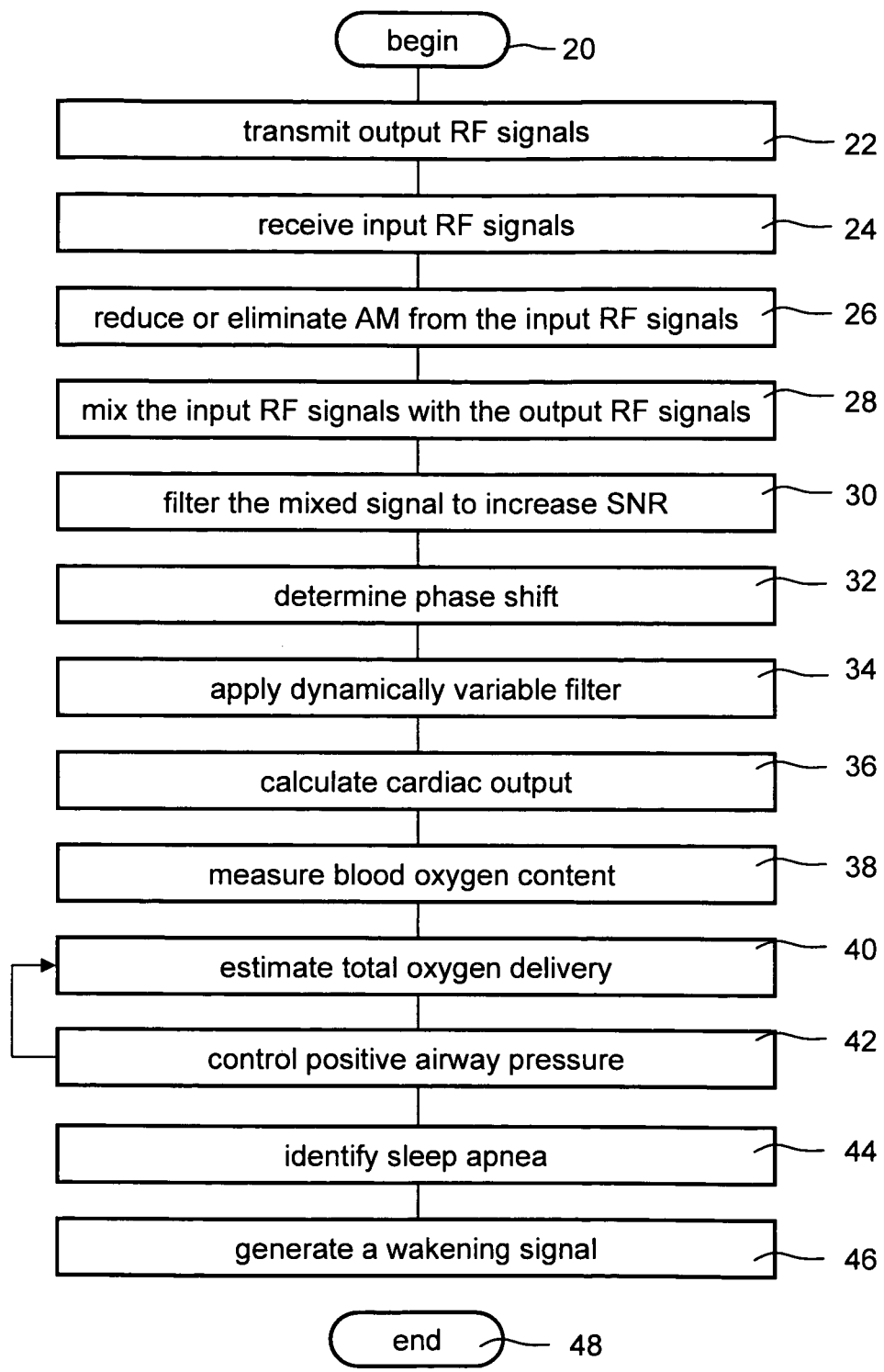
FIG. 3 is a flowchart diagram of a more detailed method suitable for monitoring sleep according to various exemplary embodiments of the present invention.

A more detailed method for monitoring sleep according to some embodiments of the present invention is illustrated in the flowchart diagram of FIG. 3.

The method begins at step 20 and optionally continues to step 22 in which output radiofrequency signals are transmitted to the subject during sleep, and step 24 in which input radiofrequency signals are received from the subject during sleep. The output radiofrequency signals can be generated by a radiofrequency generator which generates a periodic high frequency current output in response to a periodic control input signal. The current output can be transmitted to the subject via an arrangement of electrodes for carrying current output from the radiofrequency generator as known in the art. The electrodes can be connected to locations of the body of the subject, e.g., above and below the heart. Since the transmission and reception of signals is done during sleep, the electrodes are optionally and preferably placed on the subject's back so as not to interfere with upper body motion.

Current, generated by the radiofrequency generator, flows across the thorax and causes a voltage drop due to the impedance of the body. The input radiofrequency signals are typically, but not obligatorily, relate to the hemodynamic reactance of an organ of the subject.

As used herein, "hemodynamic reactance" refers to the imaginary part of the impedance. Techniques for extracting the imaginary part from the total impedance are known in the art. Typically, such extraction is performed at hardware level but the use of algorithm at a software level is not excluded from the scope of the present invention.

According to some embodiments of the present invention the method continues to step 26 in which amplitude modulation of the input radiofrequency signals is reduces or, more preferably, eliminated. Optionally and preferably the phase modulation of the signals is maintained. The input radiofrequency signals typically carry a substantial amount of AM noise, which can be described, without limitation as a signal $v(t)\cos(\omega t+\phi(t))$, which contains both phase and amplitude modulation. According to some embodiments the method generates signals having a substantial constant envelope, e.g., $v_0 \cos(\omega t+\phi(t))$, where $v_0$ is substantially a constant. The obtained signals thus represent the phase (or frequency) modulation of the input radiofrequency signal. The reduction or elimination of the amplitude modulation can be achieved, for example, using a limiter amplifier which amplifies the radiofrequency signals and limits their amplitude such that the amplitude modulation is removed.

In some embodiments, the method proceeds to step 28 in which the output radiofrequency signals are mixed with the input radiofrequency signals so as to provide a mixed radiofrequency signal. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by multiplying the input and output signals. Since a multiplication between two frequencies is equivalent to a frequency sum and a frequency difference, the mix signal is composed of the desired radiofrequency sum and radiofrequency difference.

One ordinarily skilled in the art would appreciate that the advantage in the production of a radiofrequency sum and a radiofrequency difference is that whereas the radiofrequency sum includes both the signal and a considerable amount of electrical noise, the radiofrequency difference is approximately noise-free.

According to a preferred embodiment of the method continues to step 30 in which a portion of the mixed signal is filtered out such that a remaining portion of the mixed signal is characterized by a signal-to-noise ratio (SNR) which is substantially higher compared to the signal-to-noise ratio of the mixed signal or input radiofrequency signal.

The method continues to step 32 in which a phase shift $\Delta\phi$ of the input radiofrequency signals relative to the output radiofrequency signals is determined. It was found by the inventors of the present invention that the phase shift of the input signals, as received from the subject, relative to the output signals as generated by the radiofrequency generator, is indicative of the cardiac output of the subject.

The advantage of using $\Delta\phi$ for determining the cardiac output is that the relation between the blood flow and $\Delta\phi$ depends on fewer measurement-dependent quantities as compared to conventional determination techniques in which the impedance is used. The phase shift can be determined for any frequency component of the spectrum of radiofrequency signals received from the organ. For example, in one embodiment, the phase shift is preferably determined from the base frequency component, in another embodiment the phase shift is preferably determined from the second frequency component, and so on. Alternatively the phase shift can be determined using several frequency components, e.g., using an appropriate averaging algorithm.

In some embodiments of the present invention the method continues to step 34 in which a dynamically variable filter is applied. The dynamically variable filter filters the data according to a frequency band which is dynamically adapted in response to a change in the physiological condition of the subject. It was found by the Inventor of the present invention that the dynamical adaptation of the frequency band to the physiological condition of the subject can significantly reduce the influence of unrelated signals on the measured property.

Thus, in the present embodiment, step 34 includes a process in which first the physiological condition of the subject is determined, then a frequency band is selected based on the physiological condition of the subject, and thereafter the input signals are filtered according to frequency band. The frequency band is dynamically adapted in response to a change in the physiological condition.

The physiological condition is preferably, but not obligatorily, the heart rate of the subject. The data pertaining to the physiological condition can be collected via a suitable data collection unit either in analog or digital form, as desired. For example, the physiological condition can be a heart rate which can be determined, e.g., by analysis of ECG signals or the like.

While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 4A:
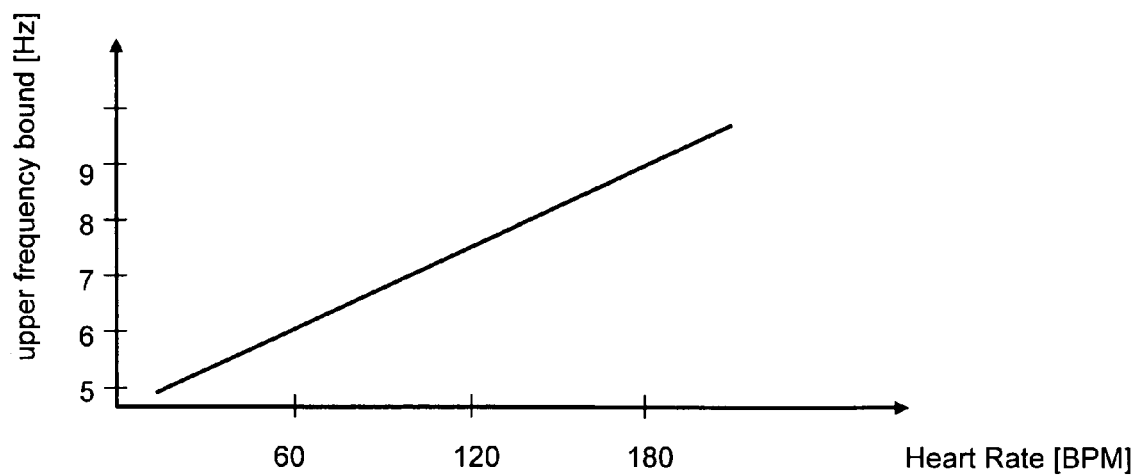
FIGS. 4a-b show a representative example of dynamically varying frequency bounds, employed according to embodiments of the present invention.
Figure 4B:
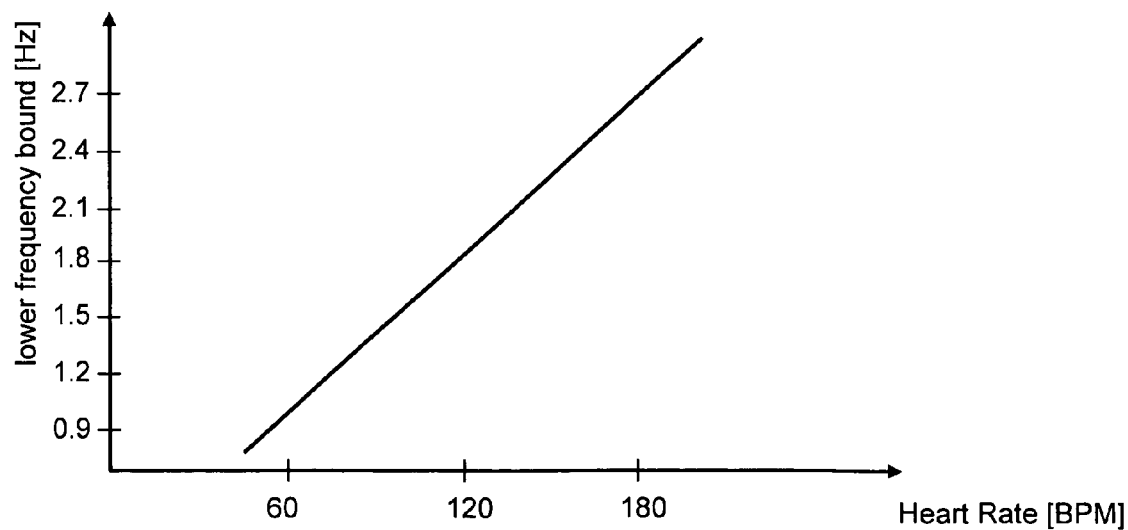

A representative example of a dynamically varying frequency bounds is illustrated in FIGS. 4a-b. Shown in FIGS. 4a-b is the functional dependence of the frequency bounds (upper bound in FIG. 4a and lower bound in FIG. 4b) on the heart rate of the subject. As shown in FIG. 4a, the upper bound of the frequency band varies linearly such that at a heart rate of about 60 beats per minute (bpm) the upper bound is about 6 Hz, and at a heart rate of about 180 bpm the upper bound is about 9 Hz. Preferably, the upper bound is about 6+1.5×[(HR/60)−1] Hz at all times, where HR is the heart rate of the subject in units of bpm. As shown in FIG. 4b, the lower bound of the frequency band varies linearly such that at a heart rate of about 60 the lower bound is about 0.9 Hz bpm and at a heart rate of about 180 bpm the lower bound is about 2.7 Hz. The lower bound is about 0.9×(HR/60) Hz at all times.

As used herein the term "about" refers to ±10%.

Figure 4C:
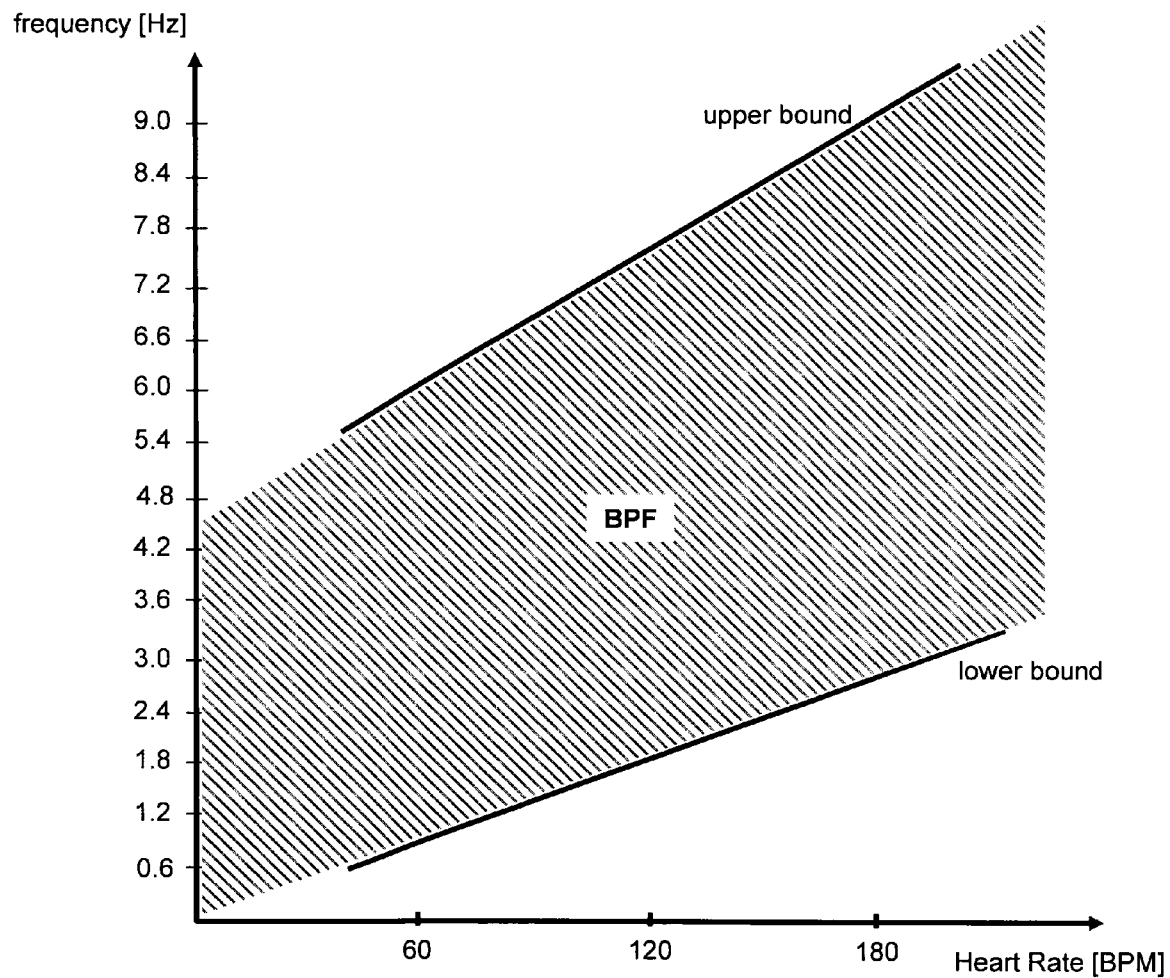
FIG. 4c show a representative example of a dynamically varying frequency band, employed according to embodiments of the present invention.

A dynamically varying band pass filter (BPF) characterized by the frequency bounds described above is illustrated in FIG. 4c. As shown, each heart rate is associated with a frequency band defined by a lower bound and an upper bound. For example, for a heart rate of 60 bpm, FIG. 4c depicts a BPF in which the lower bound is about 0.9 Hz and the upper bound is about 6 Hz.

It is to be understood that the values presented above and the functional relations illustrated in FIGS. 4a-b are exemplary embodiments and should not be considered as limiting the scope of the present invention in any way. In other exemplary embodiments, the functional relations between the frequency band and the physiological condition can have different slopes and/or offsets, or they can be non-linear.

The method continues to step 36 in which the cardiac output is calculated, based on $\Delta\phi$. It was found by the inventor of the present invention that there is a linear relationship between $\Delta\phi$ and the cardiac output, with a proportion coefficient comprising the systolic ejection time, T. For example, the cardiac output CO can be calculated using the relation CO=const.×T×$\Delta\phi$×HR, where HR is the heart rate of the subject (e.g., in units of beats per minutes), and "const." is a constant which can be found, for example, using a calibration curve.

In some embodiments of the present invention, the method continues to step 38 in which blood oxygen content is measured. This can be done, for example, using a conventional non-invasive pulse oximeter, which provides an approximation of the saturation of oxyhemoglobin ($SpO_2$). Optionally, the method estimates or receives as input the hemoglobin concentration of the sleeping subject, and uses the hemoglobin concentration to estimate blood oxygen content. The blood oxygen content can be supplemented to the calculated cardiac output for the purpose of improving sensitivity and/or specificity. In some embodiments of the present invention the method continues to step 40 in which the total oxygen delivery is estimated. The total oxygen delivery can be estimated by combining the cardiac output, oxyhemoglobin saturation and hemoglobin concentration. For example, total oxygen delivery rate (typically expressed in units of mL of oxygen per minute) can be estimated by multiplying the cardiac output by the oxygen content.

In some embodiments of the present invention the method continues to step 42 in which positive airway pressure delivered to the subject is controlled, based on the estimated value of the total oxygen delivery. In various exemplary embodiments of the invention the control of airway pressure is in a closed loop feedback with the estimation of total oxygen delivery. Thus, the method controls the delivered positive airway pressure such as to ensure that the estimated amount of total oxygen delivery rate is above a predetermined threshold, or within a predetermined range.

The method continues to step 44 in which the calculated cardiac output is used for identifying sleep apnea events. Generally, sleep apnea events correlate with a significantly fast drop in the cardiac output (see the non limiting example of FIG. 2). Thus, according to the a preferred embodiment of the present invention, when the cardiac output is reduced by a predetermined percentage over a sufficiently short and predetermined time period, the method identifies sleep apnea event. In various exemplary embodiments of the invention an apnea event is identified when the cardiac output is reduced by at least 30%, more preferably at least 40%, more preferably at least 50% over a time period of less than two minutes. Upon identification of an apnea event the method optionally generate a wakening signal (step 46).

When other quantities are measured and/or estimated, these quantities are optionally and preferably used together with the calculated cardiac output for identifying sleep apnea events. Addition of other quantities may aid in reducing false positive and false negative identification solely based on cardiac output alone. For example, blood oxygen content can be supplemented to the cardiac output, wherein a sleep apnea event can be identified when there is a predetermined drop in cardiac output and a predetermined drop in oxygen content.

When the total oxygen delivery is estimated by the method, the estimated value can be used to identify apnea event and/or to asses subject condition. For example, when the total oxygen delivery falls below a predetermined threshold which can be expressed as percentage of baselines, the method can generate a wakening alarm sensible by the sleeping subject or control a CPAP device to increase pressure.

The method ends at step 48.

Figure 5:
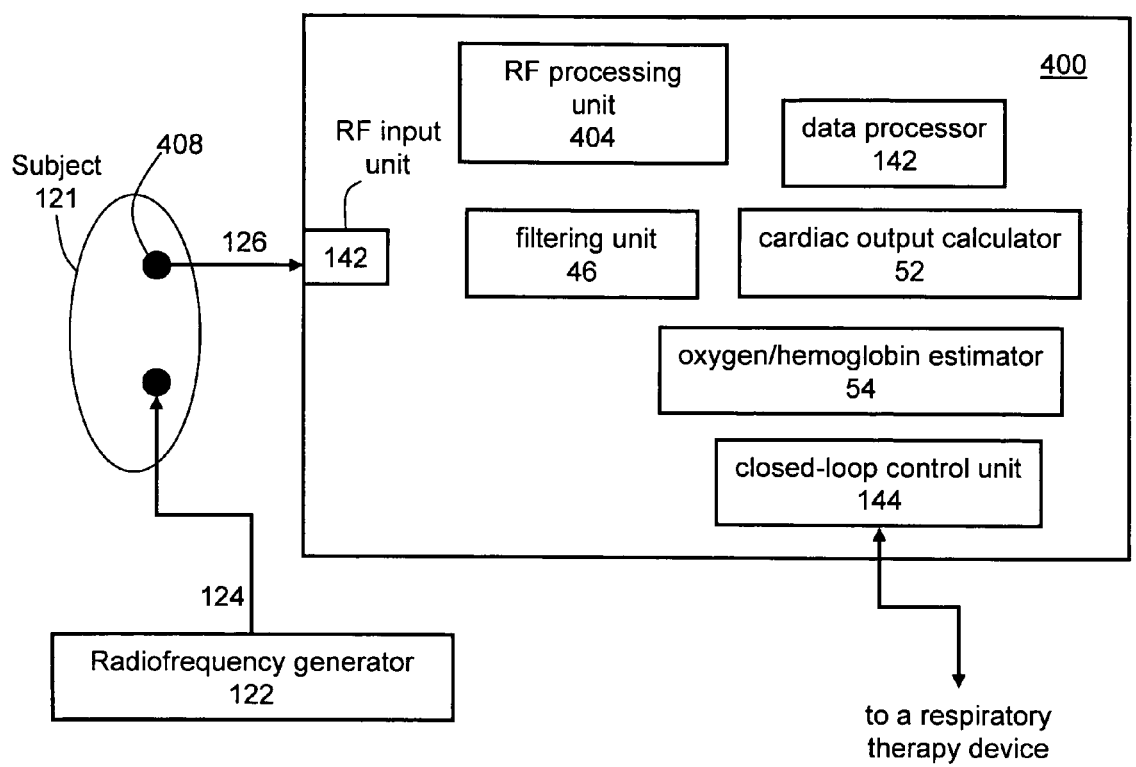
FIG. 5 is a schematic illustration of apparatus for monitoring sleep, according to various exemplary embodiments of the present invention.

Reference is now made to FIG. 5 which is a schematic illustration of apparatus 400 for monitoring sleep of a sleeping subject 121, according to various exemplary embodiments of the present invention.

Apparatus 400 comprises an input unit 142 for receiving input radiofrequency signals sensed from the organ. The input radiofrequency signals typically comprise radiofrequency signals related to the electrical properties of the organ (e.g., bioimpedance which may generally relate to the impedance and/or hemodynamic reactance of the organ). The signals are sensed from one or more sensing locations 408 on the organ of subject 121 and are originated by output radiofrequency signals 124 generated by a radiofrequency generator 122.

Apparatus 400 further comprises a signal processing unit 404 which processes the input radiofrequency signals. The processing may include, for example, mixing, demodulation, determination of phase shift, analog filtering, sampling and any combination thereof. Signal processing unit 404 may or may not be in communication with radiofrequency generator 122, as desired. A representative example of signal processing unit 404 is provided hereinunder with reference to FIG. 6.

Apparatus 400 is optionally and preferably designed for determining a phase shift Δϕ of signals 126 relative to signals 124. This can be done using a phase shift determinator 50 (not shown, see FIG. 6) which can operate according to any known technique for determining a phase shift. The phase shift can be determined for any frequency component of the spectrum of radiofrequency signals received from the organ. For example, in one embodiment, the phase shift is determined from the base frequency component, in another embodiment the phase shift is determined from the second frequency component, and so on. Alternatively the phase shift can be determined using several frequency components, e.g., using an appropriate averaging algorithm.

The input radiofrequency signals may include one or more noise components, which may be introduced into the signal due to various reasons, e.g., subject agitation or breathing. In various exemplary embodiments of the invention apparatus 400 is capable of reducing or eliminating these noise components. In some embodiments of the present invention apparatus 400 further comprises a filtering unit 406 which filters the processed input signals. Unit 406 preferably performs the filtration operation in the frequency domain. Thus, in various exemplary embodiments of the invention, a series of samples of the processed radiofrequency signals are transformed, e.g., by a Fast Fourier Transform (FFT), to provide a spectral decomposition of the signals in the frequency domain. The transformation to the frequency domain can be done by a data processor. Algorithms for performing such transformations are known to those skilled in the art of signal processing.

The obtained spectral decomposition of the signal is filtered by unit 406 which typically eliminates one or more of the frequencies in the spectrum, depending on the upper and lower frequency bounds of the filter employed by unit 406. Unit 406 preferably employs a dynamically variable filter, such as, but not limited to, the dynamically variable filer described hereinabove.

In some embodiments of the present invention apparatus 400 comprises a cardiac output calculator 52 which calculates the cardiac output as further detailed hereinabove. Optionally, apparatus 400 comprises an estimator 54 which estimates total oxygen delivery as further detailed hereinabove. Estimator 54 can communicate with a blood oxygen measuring device (not shown, see FIG. 8) and receive oxygen data therefrom for the purpose of performing the estimations. Estimator 54 can also receive hemoglobin concentration as input and use the hemoglobin concentration in combination with data received from the blood oxygen measuring device to estimate the oxygen content. For example, when the blood oxygen measuring device provides saturation data, such as arterial oxygen saturation, the oxygen content can be estimated as the product of arterial oxygen saturation, hemoglobin concentration and a constant, which reflects the hemoglobin-oxygen binding capacity.

A sleep apnea identification unit 56 uses the calculated cardiac output and identifies sleep apnea events as further detailed hereinabove. In embodiments in which estimator 54 is employed unit 56 optionally and preferable uses the estimated quantity (oxygen content, total oxygen delivery) in combination with the calculated cardiac output for identifying sleep apnea events. Unit 56 can also be configured to receive oxygen content data from a blood oxygen measuring device or from estimator 54 and use the oxygen content data in combination with the calculated cardiac output for identifying sleep apnea events. Calculator 52 and estimator 54 can be associated with a data processor 142. Data processor 142 can also be employed by unit 406 for performing the transformation to the frequency domain and/or eliminating the frequency components according to the dynamically variable frequency bounds.

Data processor 142 can also be configured for calculating other quantities, e.g., stroke volume and/or other blood-volume related quantities.

Optionally, apparatus 400 comprises a closed-loop control unit 144 which receives the estimated value of total oxygen delivery from estimator 54 and controls pressure delivered by a respiratory therapy device (not shown, see FIG. 8) based on the estimated value. In various exemplary embodiments of the invention closed-loop control unit 144 controls the pressure to ensure that the estimated value of total oxygen delivery is above a predetermined threshold or within a predetermined range.

Figure 6:
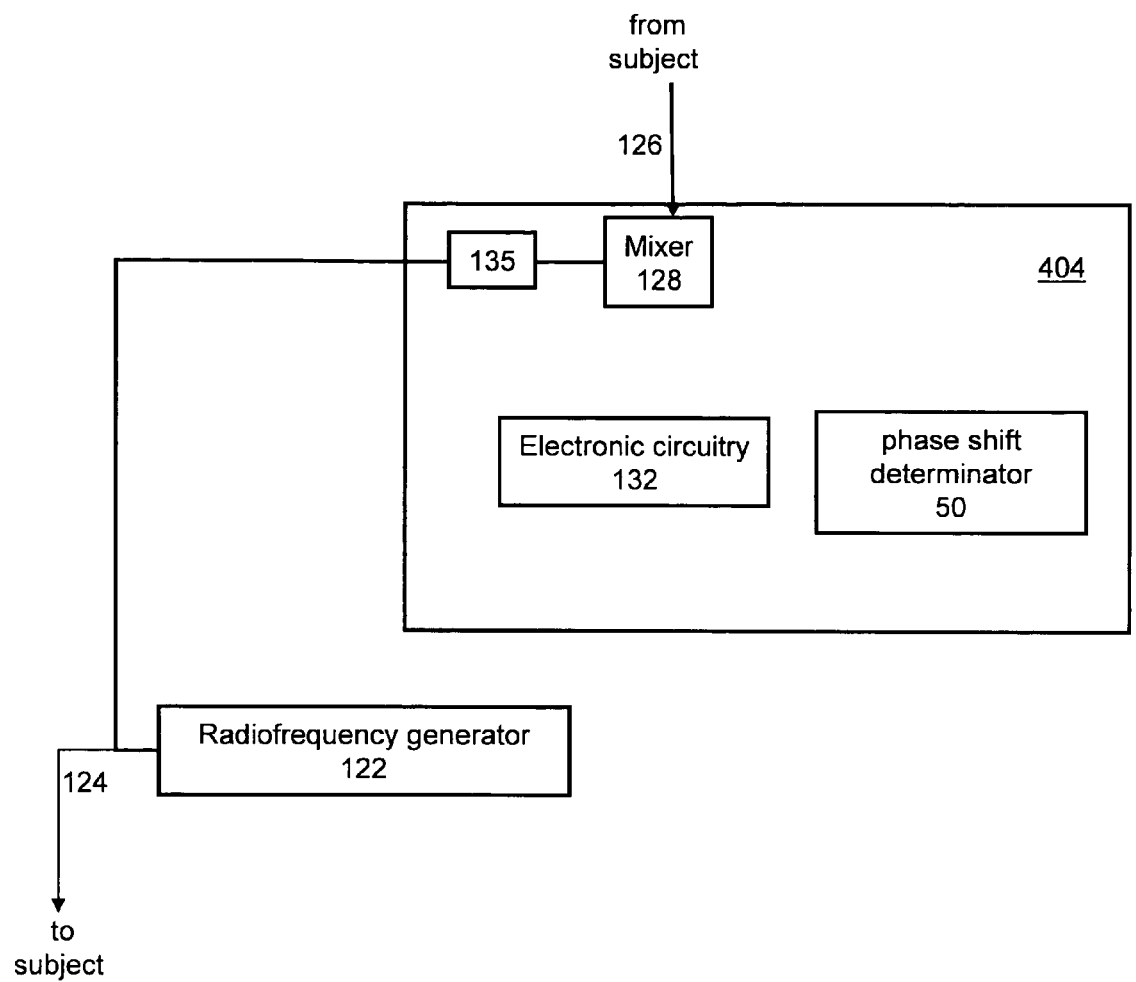
FIG. 6 is a schematic illustration of a signal processing unit, according to various exemplary embodiments of the present invention.

Reference is now made to FIG. 6 which schematically illustrates signal processing unit 404, according to various exemplary embodiments of the present invention. Unit 404 preferably comprises a mixer 128, electrically communicating with generator 122, for mixing output signals 124 and input signals 126, so as to provide a mixed radiofrequency signal. Signals 124 and 126 may be inputted into mixer 128 through more than one channel, depending on optional analog processing procedures (e.g., amplification) which may be performed prior to the mixing.

Mixer 128 may be any known radiofrequency mixer, such as, but not limited to, double-balanced radiofrequency mixer and unbalanced radiofrequency mixer. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by selecting mixer 128 such that signals 124 and signals 126 are multiplied thereby. Since a multiplication between two frequencies is equivalent to a frequency sum and a frequency difference, mixer 128 outputs a signal which is composed of the desired radiofrequency sum and radiofrequency difference.

According to various exemplary embodiments of the present invention unit 404 further comprises a phase shift determinator 50 for determining the phase shift of the input signals relative to the output signal. Phase shift determinator 50 can determine the phase shift according to any technique known in the art. For example, the phase shift can be determined from the radiofrequency difference outputted from mixer 128.

According to a preferred embodiment of the present invention processing unit 404 further comprises electronic circuitry 132, which filters out a portion of the signal such that a remaining portion of the signal is characterized by a substantially increased signal-to-noise ratio.

Figure 7:
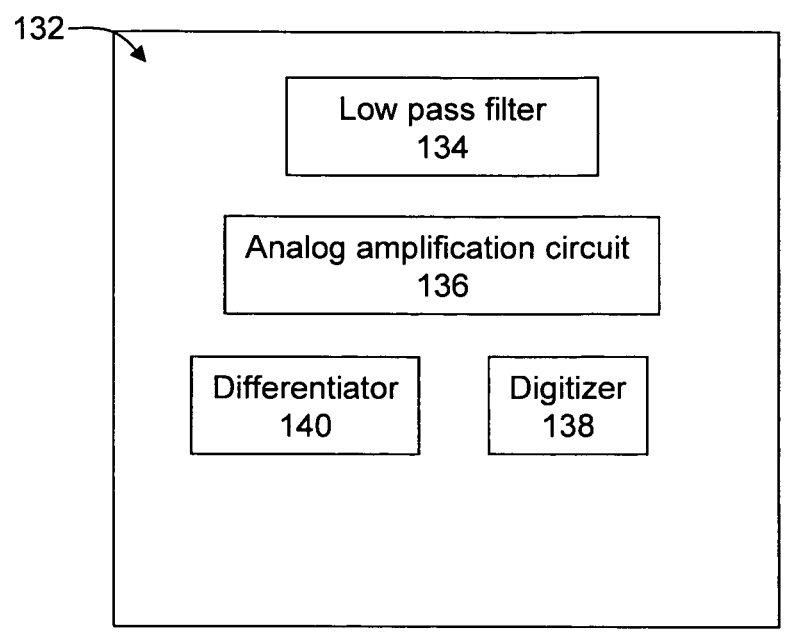
FIG. 7 is a block diagram of electronic circuitry, according to various exemplary embodiments of the present invention.

Circuitry 132 is better illustrated in FIG. 7. According to an embodiment of the present invention circuitry 132 comprises a low pass filter 134 to filter out the high frequency content of the signal. Low pass filter 134 is particularly useful in the embodiment in which mixer 128 outputs a sum and a difference, in which case low pass filter 134 filters out the radiofrequency sum and leaves the approximately noise-free radiofrequency difference. Low pass filter 134 may be designed and constructed in accordance with the radiofrequency difference of a particular system which employs apparatus 400. A judicious design of filter 134 substantially reduces the noise content of the remaining portion.

Circuitry 132 preferably comprises an analog amplification circuit 136 for amplifying the remaining portion of the signal. The construction and design of analog amplification circuit 136 is not limited, provided circuit 136 is capable of amplifying the signal. Amplification circuits suitable for the present embodiments are found in International Patent Application, Publication Nos. WO 2004/098376 and WO 2006/087696 the contents of which are hereby incorporated by reference.

According to a preferred embodiment of the present invention circuitry 132 further comprises a digitizer 138 for digitizing the signal. The digitization of the signal is useful for further digital processing of the digitized signal, e.g., by a microprocessor.

Optionally, circuitry comprises a differentiator 140 (either a digital differentiator or an analog differentiator) for performing at least one time-differentiation of the measured impedance to obtain a respective derivative (e.g., a first derivative, a second derivative, etc.) of the bioimpedance or hemodynamic reactance. Differentiator 140 may comprise any known electronic functionality (e.g., a chip) that is capable of performing analog or digital differentiation.

According to a preferred embodiment of the present invention signal processing unit 404 comprises an envelope elimination unit 135 which reduces or, more preferably, eliminates amplitude modulation of signals 126. Optionally and preferably, unit 135 maintains the phase modulation of signals 126. The output of unit 135 represents the phase (or frequency) modulation of signal 126, as further detailed hereinabove. Unit 135 can employ, for example, a limiter amplifier which amplifies signals 126 and limits their amplitude such that the amplitude modulation is removed. The advantage of the removal of the amplitude modulation is that it allows a better determination of the phase shift $\Delta\phi$ between the input and output signals, as further detailed hereinabove.

Figure 8:
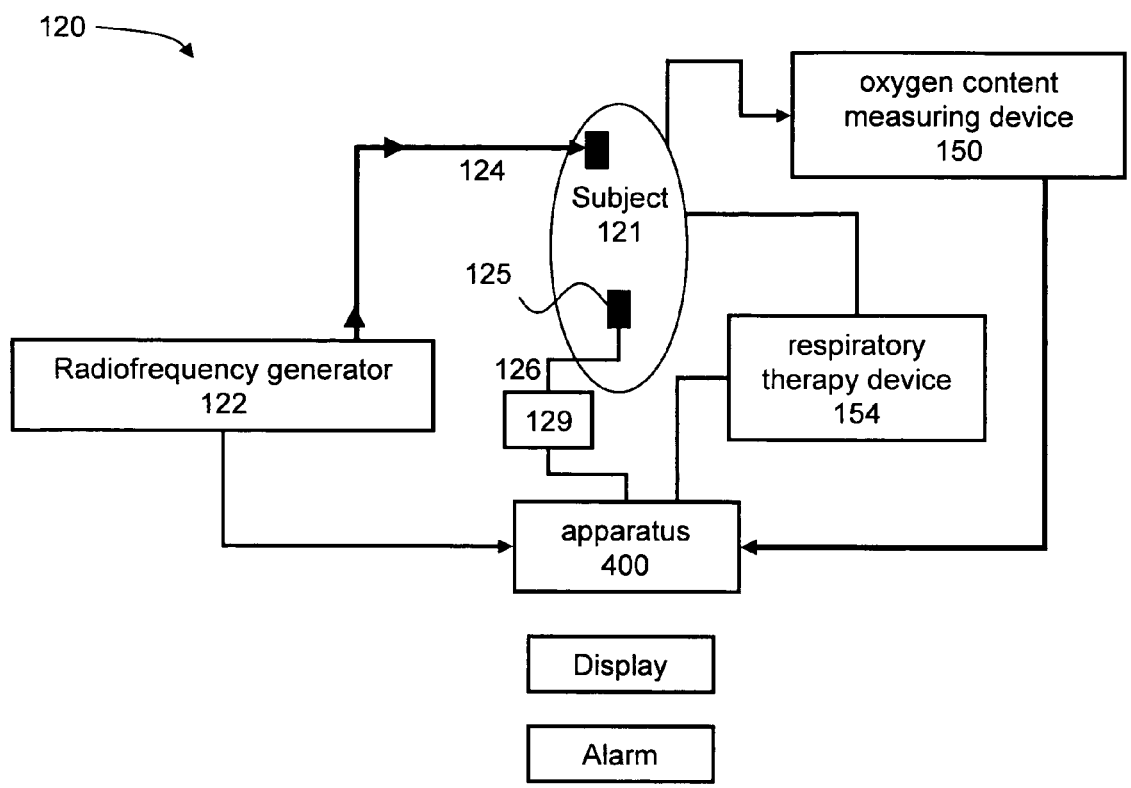
FIG. 8 is a schematic illustration of a system for monitoring sleep of a sleeping subject.

Reference is now made to FIG. 8, which is a schematic illustration of system 120 for monitoring sleep of a subject, according to a preferred embodiment of the present invention. System 120 preferably comprises a radiofrequency generator 122, for generating output radiofrequency signals. Generator 122 may be embodied as any radiofrequency generator. System 120 further comprises a plurality of electrodes 125, which are connected to the skin of subject 121. Electrodes 125 transmit output radiofrequency signals 124, generated by generator 122 and sense input radiofrequency signals 126 originated from the organ of subject 121.

System 120 preferably comprises any of the components of apparatus 400 described above. According to a preferred embodiment of the present invention system 120 further comprises a detector 129 for detecting a voltage drop on a portion of the body of subject 121 defined by the positions of electrodes 125. In response to the detected voltage, detector 129 preferably generates signals which are indicative of impedance of the respective portion of the body. In this embodiment, the stroke volume can be calculated using $(dX/dt)_{max}$, as further detailed hereinabove. Knowing the stroke volume, the cardiac output is calculated by multiplying the stroke volume by the heart rate of the subject. More preferably, detector 129 generates signals which are indicative of a hemodynamic reactance, X.

In some embodiments, system 120 comprises a blood oxygen measuring device 150 which provides apparatus 400 with oxygen data via a communication line 152. Device 150 can be, for example, a conventional pulse oximeter or the like. Apparatus 400 combines the calculated cardiac output with the oxygen content data for identifying sleep apnea as further detailed hereinabove. The system In some embodiments of the present invention can comprise a display for displaying status of sleep (e.g., continually showing cardiac output and/or total oxygen delivery). The system can also comprise an alarm device for generating a wakening signal. The alarm preferably communicates with apparatus 400 which signals the alarm to generate the awakening signal upon occurrence of a sleep apnea event or when the total oxygen delivery is below a predetermined threshold.

System 120 can also comprise a respiratory therapy device 154, such as, but not limited to, a continuous positive airway pressure (CPAP) device. Device 154 can comprise a blower connected through a hose and a mask, such as a nasal mask or a nasal cannula, to the patient's respiratory airway. Device 54 can also include an air flow sensor and an air pressure sensor. Device 154 can be controlled by apparatus 400 (e.g., via the closed-loop control unit 144, see FIG. 5) so as to ensure that the estimated oxygen delivery rate is above a predetermined threshold or within a predetermined range. Thus, a closed loop feedback can be established so as to continuously monitor the oxygen delivery as estimated by apparatus 400 and the pressure of air flow delivered by device 154, and to vary the pressure to accord with the estimated oxygen delivery.

Following are technical preferred values which may be used for selective steps and parts of the embodiments described above.

The output radiofrequency signals are preferably from about 10 KHz to about 200 KHz in frequency and from about 10 mV to about 200 mV in magnitude; the input radiofrequency signals are preferably about 75 KHz in frequency and about 20 mV in magnitude; a typical impedance which can be measured by the present embodiments is from about 5 Ohms to about 75 Ohms; the resulting signal-to-noise ratio of the present embodiments is at least 40 dB; low pass filter 134 is preferably characterized by a cutoff frequency of about 35 Hz and digitizer 138 preferably samples the signals at a rate of about 500-1000 samples per second.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of monitoring sleep of a sleeping subject using output radiofrequency signals transmitted to the subject during sleep and input radiofrequency signals received from the subject during sleep, the method comprising:
   determining a phase shift of the input radiofrequency signals relative to the output radiofrequency signals to provide processed signals;
   applying to said processed signals a dynamically variable filter characterized by a frequency band which is dynamically adapted in response to a change in a physiological condition of the subject;
   using a cardiac output calculator, calculating cardiac output based on said filtered processed signals; and
   using said cardiac output for identifying sleep apnea events.

2. The method of claim 1, further comprising supplementing said cardiac output with blood oxygen content, wherein said identification of said sleep apnea events is based on said cardiac output and said blood oxygen content.

3. The method of claim 1, further comprising inputting or estimating hemoglobin concentration of the sleeping subject, wherein said identification of said sleep apnea events is based on said cardiac output and said hemoglobin concentration.

4. The method of claim 3, further comprising estimating total oxygen delivery and generating a wakening signal when an estimated value is below a predetermined threshold.

5. The method of claim 4, wherein said identification of said sleep apnea events is further based on said estimated value of said total oxygen delivery.

6. The method of claim 4, further comprising controlling positive airway pressure delivered to the sleeping subject based on said estimated value.

7. The method of claim 1, further comprising reducing or eliminating amplitude modulation of said input radiofrequency signals so as to provide input radiofrequency signals of substantially constant envelope.

8. The method of claim 1, further comprising mixing said output radiofrequency signals and said input radiofrequency signals so as to provide a mixed radiofrequency signal, and filtering out a portion of said mixed radiofrequency signal so as to substantially increase a signal-to-noise ratio of a remaining portion of said mixed radiofrequency signal.

9. The method of claim 1, wherein said cardiac output is calculated using a linear relationship between said filtered processed signals and said cardiac output.

10. The method of claim 1, wherein said physiological condition is a heart rate of the subject.

11. The method of claim 10, wherein a lower frequency bound characterizing said filter is about 0.9*(HR/60) Hz at all times, wherein said HR is said heart rate in units of beats per minute.

12. The method of claim 10, wherein an upper frequency bound characterizing said filter is about 6+1.5*[(HR/60)−1] Hz at all times, wherein said HR is said heart rate in units of beats per minute.

13. A method of monitoring sleep of a sleeping subject, comprising:
  transmitting output radiofrequency signals to the subject during sleep;
  receiving input radiofrequency signals from the subject during sleep; and
  executing the method of claim 1.

14. The method of claim 13, further comprising measuring blood oxygen content and supplementing said cardiac output with blood oxygen content, wherein said identification of said sleep apnea events is based on said cardiac output and said blood oxygen content.

15. Apparatus for monitoring sleep of a sleeping subject using output radiofrequency signals transmitted to the subject during sleep and input radiofrequency signals received from the subject during sleep, the apparatus comprising:
  a phase shift determinator configured for determining a phase shift of the input radiofrequency signals relative to the output radiofrequency signals, to provide processed signals;
  a filtering unit configured for applying to said processed signals a dynamically variable filter characterized by a frequency band which is dynamically adapted in response to a change in a physiological condition of the subject;
  a cardiac output calculator configured for calculating cardiac output based on said filtered processed signals; and
  a sleep apnea identification unit configured for identifying sleep apnea events based on said cardiac output.

16. The apparatus of claim 15, wherein the apparatus further comprises a total oxygen delivery estimator configured for estimating total oxygen delivery.

17. The apparatus of claim 16, wherein said sleep apnea identification unit is configured to identify said sleep apnea events based on an estimated value of said total oxygen delivery and said cardiac output.

18. The apparatus of claim 16, wherein the apparatus further comprises a closed-loop control unit configured for receiving an estimated value of said total oxygen delivery and controlling pressure delivered by a respiratory therapy device based on said estimated value.

19. The apparatus of claim 15, wherein the apparatus further comprises an envelope elimination unit designed and configured for reducing or eliminating amplitude modulation of said input radiofrequency signals so as to provide input radiofrequency signals of substantially constant envelope.

20. The apparatus of claim 15, wherein the apparatus further comprises:
  a mixer configured for mixing said output radiofrequency signals and said input radiofrequency signals, to provide a mixed radiofrequency signal; and
  a radiofrequency filter for filtering out a portion of said mixed radiofrequency signal so as to substantially increase a signal-to-noise ratio of a remaining portion of said mixed radiofrequency signal.

21. The apparatus of claim 15, wherein a lower frequency bound characterizing said filter is about 0.9*(HR/60) Hz at all times, wherein said HR is said heart rate in units of beats per minute.

22. The apparatus of claim 15, wherein an upper frequency bound characterizing said filter is about 6+1.5*[(HR/60)−1] Hz at all times, wherein said HR is said heart rate in units of beats per minute.

23. A system for monitoring sleep of a sleeping subject, comprising:
  a radiofrequency generator for generating output radiofrequency signals;
  a plurality of electrodes designed for transmitting said output radiofrequency signals to the subject and for sensing input radiofrequency signals from the subject; and
  the apparatus of claim 15.

24. The system of claim 23, further comprising a blood oxygen measuring device.

25. The system of claim 23, wherein the apparatus further comprises a total oxygen delivery estimator configured for estimating total oxygen delivery, and wherein the apparatus further comprises a closed-loop control unit configured for receiving an estimated value of said total oxygen delivery and controlling pressure delivered by a respiratory therapy device based on said estimated value.

26. The system of claim 25, further comprising said respiratory therapy device.

* * * * *